(12) United States Patent
Siebecke et al.

(10) Patent No.: US 9,708,271 B2
(45) Date of Patent: Jul. 18, 2017

(54) EXTRACTION REACTOR AND ALSO METHOD FOR EXTRACTION FROM GRANULAR MATERIAL

(71) Applicant: Uhde Inventa-Fischer GmbH, Berlin (DE)

(72) Inventors: Ekkehard Siebecke, Berlin (DE); Johannes Katzer, Berlin (DE); Bernd Königsmann, Langewahl (DE); Mirko Bär, Birkenwerder (DE)

(73) Assignee: Uhde Inventa-Fischer GmbH, Berlin (DE)

( * ) Notice: Subject to any disclaimer, the term of this patent is extended or adjusted under 35 U.S.C. 154(b) by 381 days.

(21) Appl. No.: 14/073,629

(22) Filed: Nov. 6, 2013

(65) Prior Publication Data

US 2014/0135491 A1    May 15, 2014

Related U.S. Application Data

(60) Provisional application No. 61/722,899, filed on Nov. 6, 2012.

(51) Int. Cl.
*B01J 19/00* (2006.01)
*C07D 223/10* (2006.01)
*C08G 69/14* (2006.01)
*C08G 69/16* (2006.01)

(52) U.S. Cl.
CPC ......... *C07D 223/10* (2013.01); *C08G 69/14* (2013.01); *C08G 69/16* (2013.01)

(58) Field of Classification Search
CPC ........ C08G 73/01; C08G 69/01; C08G 69/46; C08G 69/28

USPC .......... 528/492, 422, 499; 422/130
See application file for complete search history.

(56) References Cited

U.S. PATENT DOCUMENTS

| | | | |
|---|---|---|---|
| 2,248,220 A | 7/1941 | Dons | |
| 2,578,670 A | 12/1951 | Carleton | |
| 3,905,946 A * | 9/1975 | Nieswandt | C08G 69/46 528/323 |
| 4,002,430 A | 1/1977 | Hoerauf | |

(Continued)

FOREIGN PATENT DOCUMENTS

| | | |
|---|---|---|
| DE | 206999 A1 | 2/1984 |
| DE | 19752182 A1 | 5/1999 |
| DE | 19801267 A1 | 7/1999 |

OTHER PUBLICATIONS

"Chinese Application Serial No. 201380058137.6, Office Action mailed Apr. 19, 2016", w/English Translation, (Apr. 19, 2016), 34 pgs.

(Continued)

*Primary Examiner* — Nina Bhat
(74) *Attorney, Agent, or Firm* — Schwegman Lundberg & Woessner, P.A.

(57) ABSTRACT

The present application relates to an extraction reactor with which granular material, in particular granular polyamide, can undergo extraction, soluble components being dissolved out of the granular material with an extraction liquid during the extraction. In the case of polyamide materials, these are for example oligomeric or monomeric components which have remained in the granular material during the polycondensation reaction for the production of the polyamide materials.

20 Claims, 5 Drawing Sheets

(56) References Cited

U.S. PATENT DOCUMENTS

| | | | | |
|---|---|---|---|---|
| 4,053,457 A | * | 10/1977 | Cordes | C08G 69/46 |
| | | | | 528/323 |
| 4,160,647 A | | 7/1979 | Sendov et al. | |
| 4,360,662 A | * | 11/1982 | Williams | C08G 63/90 |
| | | | | 528/191 |
| 4,978,743 A | * | 12/1990 | Selbeck | C08G 69/46 |
| | | | | 422/129 |
| 6,179,958 B1 | * | 1/2001 | Lysen | D21C 1/02 |
| | | | | 162/15 |
| 6,320,021 B1 | * | 11/2001 | Hildenbrand | C08G 69/16 |
| | | | | 528/310 |
| 6,326,457 B1 | * | 12/2001 | Erbes | B01D 11/0242 |
| | | | | 528/310 |
| 6,326,460 B1 | * | 12/2001 | Mohrschladt | C08G 69/04 |
| | | | | 528/422 |
| 7,753,080 B2 | * | 7/2010 | Liu | B01F 5/061 |
| | | | | 138/39 |
| 2002/0183478 A1 | | 12/2002 | Fergusson et al. | |

OTHER PUBLICATIONS

"European Application Serial No. 12 191 455.0, Office Action mailed Apr. 21, 2016", w/English Translation, (Apr. 21, 2016), 20 pgs.

"International Application No. PCT/EP2013/071987, International Preliminary Report on Patentability mailed May 12, 2015", w/English Translation, (May 12, 2015), 9 pgs.

"International Application No. PCT/EP2013/071987, International Search Report mailed Jan. 22, 2014", w/English Translation, (Jan. 22, 2014), 9 pgs.

"International Application No. PCT/EP2013/071987, Written Opinion mailed Jan. 22, 2014", w/English Translation, (Jan. 22, 2014), 18 pgs.

* cited by examiner

EXTRACTION REACTOR AND ALSO METHOD FOR EXTRACTION FROM GRANULAR MATERIAL

CLAIM OF PRIORITY

This patent application claims the benefit of priority to U.S. Provisional Patent Application Ser. No. 61/722,899, entitled "EXTRAKTIONSREAKTOR SOWIE VERFAHREN ZUR EXTRAKTION VON GRANULÄREM MATERIAL," filed on Nov. 6, 2012, which is hereby incorporated by reference herein in its entirety.

OVERVIEW

The present disclosure relates to an extraction reactor with which granular material, for example, granular polyamide, can undergo extraction. During the extraction, soluble components can be dissolved out of the granular material with an extraction liquid. In the instance of polyamide materials, these are, for example, oligomeric or monomeric components which have remained in the granular material during a polycondensation reaction for the production of the polyamide materials.

The oligomers (OM) and monomers of the raw material caprolactam (and OM of the raw materials which are required for the production of copolymers) which remain in the melt during the polycondensation of polyamide 6 (or polyamide 6 with a copolymer proportion <30%), are separated in a subsequently connected extraction unit. The content of OM can be above 6% by mass and the separation can be implemented by means of a one or multistep extraction process. The polymer, which is cooled and comminuted to form granulate, is guided in counterflow to an extraction liquid (e.g., water with varying levels of caprolactam contents). The extraction liquid thereby absorbs the monomers and oligomers (extractable materials) from the polymer granulate, the entire content of extractable materials in the granulate can be reduced to below 1% by mass. The extraction liquid which remains in the polymer instead of the extractable materials can be removed in a subsequent drying step. The flow control is generally such that the granulate is guided through the extraction container from top to bottom in a percolation bed, the extraction liquid being conducted from the bottom to the top. A uniform flow of granulate and extraction liquid is intended to be ensured by means of baffles.

Because of the different solubility of monomers and oligomers in the extraction liquid, the extraction is frequently implemented in two (or more) steps. In a first step, the oligomers are separated with a suitable extraction liquid (e.g., water with a caprolactam proportion of 5 to 50% by mass). In an example, the extraction liquid can include water with a caprolactam proportion of about 12 to about 25% by mass. In one (or more) further extraction steps, the monomers and the residually remaining oligomers are removed from the polymer by means of an extraction liquid (e.g., water with a caprolactam proportion of below 0.5% by mass). In an example, the monomers and the residually remaining oligomers can be removed from the polymer by means of extraction liquid including water with a caprolactam proportion of below 0.1% by mass.

During the extraction of monomers and oligomers from polyamide 6 (with or without copolymers), a strong dependency upon the extraction temperature is established. Basically, it can be said that, at increased temperatures, the extraction speed and effectiveness increases greatly. In practice, an extraction temperature which is slightly below the atmospheric boiling temperature of the extraction liquid is set.

The maximum extraction temperature which should not be exceeded during the liquid extraction is prescribed by the hydrolysis of the polyamide 6 at high temperatures in an aqueous environment. In order to avoid damage to the polymer, an extraction temperature of 140° C. (and for example 130° C.) can be used when using water with a caprolactam content of up to 25% by mass as the extraction liquid. In an example, dwell times of more than 1 hour, should be avoided.

A further limiting factor for the extraction temperature is the local boiling temperature inside the extraction column which is prescribed by the hydrostatic pressure. In an example, the local boiling temperature should not be exceeded in order to avoid negative process effects.

For a further increase in the extraction temperature above the atmospheric boiling point of the extraction liquid, several possibilities are made use of. For example:

1. Use of the hydrostatic height of the extraction reactor, temperature of the extraction liquid in the inflow is slightly below the local boiling temperature of the extraction liquid in the inflow to the extraction column but above the atmospheric boiling temperature at the top of the extraction column. Cooling of the extraction liquid by the granulate flowing in counterflow so that, in the outflow, the temperature of the extraction liquid is at all times below the atmospheric boiling temperature. When using a pre-extraction container for the oligomer separation, the entry temperature of the granulate is however so high that cooling of the extraction liquid can scarcely be effected. The effectiveness is low since only slight superheating of the incoming extraction liquid is possible. The extraction is effected in a pressureless container.

As a result of lower temperature and increasing monomer concentration in the upper part of the extractor, the density of the extraction liquid increases. There is the danger of a flow reversal in which the heavy liquid from the upper part of the extractor flows rapidly into the lower part of the extractor. The flow distribution of the granulate is disrupted and a non-uniform dwell time distribution results with quality losses.

2. Use of the hydrostatic height of the extraction reactor, temperature of the extraction liquid in the inflow is significantly above the atmospheric boiling temperature of the extraction liquid at the head of the extraction column, however below the local boiling temperature. In the middle region of the extractor, a part of the extraction liquid is drawn off and cooled outside the extractor. Thereafter, the liquid flow is fed in again into the extractor above the removal point, whereupon the result is a mix temperature of the extraction liquid which is equal to or less than the local boiling temperature of the extraction liquid (see e.g. US-2010/0048860A1). As a result, a maximum extraction temperature of more than 120° C. can be reached in the lower part of the extractor, the result is in practice a 2-step extraction. The effectiveness of the extraction is high since the lower part of the extractor can be operated at high temperature. The extraction is effected in a pressureless container.

As a result of a significantly lower temperature and increasing monomer concentration in the upper part of the extractor, the density of the extraction liquid increases greatly. The result is a clear temperature limit which also significantly increases the danger of a flow reversal, compared to the method according to 1. There results therefrom a risk to the operating personnel since superheated liquid flows to the surface and spontaneously boils vigorously there. The flow distribution of the granulate is disrupted and the result is a non-uniform dwell time distribution with quality losses.

3. Operation of the extraction reactor as pressure extraction. The granulate from a pre-extraction step is pumped into the extractor by means of pump pressure, a higher temperature can be set there because of the higher pressure over the entire course of the extraction (see DE 10124579A1) without local boiling resulting. Very high effectiveness of the extraction results therefrom since the temperature can be raised over the entire height of the extractor. Higher complexity and costs result because of the design of the extractor as a pressure container.

As a result of lower temperature and increasing monomer concentration in the upper part of the extractor, the density of the extraction liquid increases. There is the danger of a flow reversal in which the heavy liquid from the upper part of the extractor flows rapidly into the lower part of the extractor. The flow distribution of the granulate is disrupted and the result is a non-uniform dwell time distribution with quality losses.

It is common to all variants that they have an internal temperature profile which depends only upon the input temperature of granulate and extraction liquid and also upon the heat losses over the surface of the extraction reactor. It is not possible to set a temperature gradient which is regulated individually, in the optimum case at any height of the extractor with a minimum difference from the local boiling temperature of the extraction liquid.

Generally, the flow control for granulate and extraction liquid inside the extractor is effected by using conical baffles (see sketch 2, from; Fourne, Franz, "Synthetische Fasern" (Synthetic Fibres), Munich, Vienna, 1995). This involves a dependency upon capacity which is proportional to the horizontal extraction area and hence to the height of the extractor. This means that the extractors have such a great constructional height at high capacities (>100 tonnes PA/day), that they have a determining influence on the height of the buildings. Thus the previous extractor construction leads, with increasing capacity, directly to extra costs in the building techniques.

The present disclosure describes an extraction reactor which offers the possibility of setting an individual temperature gradient over the height of the extraction reactor. This should be automatically controllable as a function of the plant capacity and of the desired monomer- and oligomer content in the end products. The maximum temperature in the extraction reactor should be, at any point, at least 0.5° C., (e.g., at least 2.0° C.) below the boiling temperature of the extraction liquid at the respective hydrostatic liquid pressure. In addition, the possibility should exist of reaching a maximum extraction temperature in the shortest possible dwell time but of not exceeding it (e.g. in order to avoid product damage due to hydrolysis).

In addition, the present disclosure provides an extraction method with which granular material based in particular on PA6 polymer can undergo extraction in an efficient manner, i.e. freed of monomeric or oligomeric components.

According to the present disclosure, there is hence an extraction reactor which is suitable in particular for liquid extraction from granular material, for example polyamides, and particularly polyamides based on polyamide 6. The extraction reactor according to the present disclosure thereby comprises at least one vertically extending flow pipe which comprises a plurality of horizontally configured heat exchanger elements which fill the cross-section of the flow pipe completely or partially and which can be flowed through by the granular material and the extraction liquid, the plurality of heat exchanger elements subdividing the flow pipe into individual vertical compartments. In addition, the extraction reactor comprises at least one top-side inlet for the granular material, at least one base-side outlet for the granular material, at least one base-side supply for extraction liquid and also at least one top-side outlet for extraction liquid.

The extraction reactor according to the present disclosure is hence configured by means of a vertical flow pipe for polyamide granulate. The granulate is guided from the top to the bottom is a filled bed. An extraction liquid is guided in counterflow. The extraction liquid is distributed, via a suitable liquid distributor at the lower end of the extraction reactor, over the cross-section of the extraction reactor. The dropping granulate and the rising liquid are distributed uniformly over the diameter by means of flow baffles (cassette bases) so that a plug flow for liquid and granulate is set.

The extraction reactor according to the present disclosure hence makes possible maximum efficiency of an extraction method implemented herewith by means of optimum volume utilisation. The following advantages can be achieved with the present disclosure. The temperature control of the extraction liquid is possible over the complete extraction bed height. Setting an individual temperature gradient with maximum efficiency when setting a temperature gradient can be effected at or slightly below the local boiling temperature of the extraction liquid. The flow control by means of cassette bases which consist of individual flow elements ensures an extraction bed height independently of the extraction capacity, which enables a small constructional height with high capacities. The temperature- and flow control can prevent reversal of the flow even in the case of a high density difference between top and base of the extraction reactor. Furthermore, it can be ensured with the extraction reactor according to the present disclosure that the flow baffles can be configured such that the resulting height of the extraction reactor is independent of the required extraction capacity.

In one example, the extraction reactor can includes at least 2 heat exchanger elements. For example, the extraction reactor can include at least 3 heat exchanger elements such as 4 to 30 heat exchanger elements or 8 to 12 heat exchanger elements.

In one example, the extraction reactor provides that the heat exchanger elements are disposed in the vertical direction. The heat exchanger elements can be equidistant from each other, and/or at a different spacing from each other.

In the case where the heat exchanger elements are at a different spacing from each other, adjustment of the spacing as a function of temperature, density and concentration gradient of the extraction liquid can be calculated and the spacings of the heat exchanger elements can be adjusted and produced in a corresponding manner. According to such an embodiment, the extraction behaviour of the extraction reactor can be adapted in detail to the respective granulate to be extracted. The heat exchanger elements can thereby be preinstalled in the extraction reactor in a fixed manner, however it is also likewise conceivable that the heat exchanger elements can be displaced in the height thereof so that the heat exchanger elements can be varied in the height thereof for different extraction purposes. In one example, the heat exchanger elements are preinstalled in a fixed manner.

The examples, for the previously mentioned heat exchanger elements can be selected from the groups consisting of cassette bases, baffle bases, pipe coil constructions and also combinations hereof. In the case of a plurality of heat exchanger elements, it can be provided that these are always selected from the same group, however it is also likewise possible to select different heat exchanger elements from the previously mentioned possibilities.

In an example, the cassette bases can be used in the case of the heat exchanger elements. The cassette bases can comprise between 9 and 96 individual flow elements which have respectively a separate space for granular material and extraction liquid and also a connected space for a medium for the heat exchange. In an example, the cassette bases can comprise between 33 and 61 individual flow elements which have respectively a separate space for granular material and extraction liquid and also a connected space for a medium for the heat exchange.

In an example, the individual flow elements thereby have a square or hexagonal cross-section in the flow direction/vertical direction and a conical granulate inflow, a through-tunnel and also a conical granulate outlet.

The cassette bases can consist of individual flow elements (square or hexagonal) which are assembled adjacently to form a complete base. The transition to the reactor wall is closed by means of adapted metal sheets. As a result, a closed heating medium space which is separated from the granulate/extraction liquid space is formed. The heating medium space can be flowed through from outside, by means of connection pipes, by heat transfer medium (e.g., water, water-alcohol or water-caprolactam mixture). As a result, each cassette base acts as heat exchanger. The configuration of the cassette bases as a combination of individual flow elements leads to independence of the extraction bed height from its diameter. The individual flow elements are designed such that they ensure evening-out of the granulate and liquid flow only as a function of density differences, flow speeds, concentration differences and spacing from the next flow element thereabove and thereunder. The diameter of the extraction reactor is thereby of no importance. In the case of an increased extraction capacity which leads to a greater diameter of the extraction reactor, the number of individual flow elements is increased, the number of cassette bases or their spacing need not be changed. A constant extraction bed height results therefrom, even with an increased the extraction capacity ($\geq 3,500$ kg/h).

In an example, the cassette bases can be assembled from individual flow elements which are installed adjacently to form an overall construction. The horizontal spacing of one cassette base from the next one situated thereabove is calculated as a function of the dimension of the individual flow elements and the density differences from overall construction to overall construction. A flow reversal can consequently be reliably avoided. Alternatively, a pipe coil construction which has an effect on the flow comparable to the above-described cassette base can be used.

In the case of a greater diameter, caused by a higher extraction capacity, the number of individual flow elements per overall construction is changed but not the dimension of the individual elements. Hence the overall height of all the flow elements inside the extraction reactor (cylindrical length of the extraction reactor) remains independent of the overall extraction capacity. Alternatively, the diameter of the pipe coil construction can be enlarged in the case of a greater diameter of the extraction reactor.

The number of cassette bases can vary, as a function of the extraction quality to be achieved and the length of the extraction reactor. For example, the number of cassette bases can be from 4 to 30 such as 8 to 12. The number of individual flow elements inside one cassette base can be between 9 and 96 such as between 33 and 61.

The supply for extraction liquid can comprise a liquid distributor with which the supplied extraction liquid can be distributed over the entire cross-section of the flow pipe. A further advantageous example of the extraction reactor provides that at least some or all of the compartments comprise a temperature sensor ($T_C$) for determining the temperature of the granular material and/or of the extraction fluid present in the respective compartment.

In addition, it is possible that each heat exchanger element can have (a) a separate inflow for a medium for the heat exchange, which has a control valve via which the quantity of medium for the heat exchange, which flows through the respective heat exchanger element, can be regulated, (b) a first separate inflow for a first medium for the heat exchange and also a second separate inflow for a second medium for the heat exchange, and first and second medium are temperature-controlled differently, respectively first and second inflow being connected in pairs to respectively one heat exchange element via a three-way valve, or (3) a separate circulation for a medium for the heat exchange with circulation pump and heat exchanger.

It can likewise be provided that a plurality of heat exchanger elements are temperature-controlled in groups. This can be affected, for example, by the plurality of heat exchanger elements. For example, 2 to 6 heat exchanger elements, such as 2 to 3 heat exchanger elements, can be arranged to form groups of heat exchanger elements, by the heat exchanger elements for each group, connected successively in series, being flowed through, beginning with the vertically uppermost heat exchanger element of each group, by a medium for the heat exchange.

A parallel supply of a plurality of heat exchanger elements with heat exchange medium is possible in the same way.

Furthermore, in an example, the plurality of heat exchanger elements, connected successively in series, is flowed through, beginning from the vertically uppermost heat exchanger element, by a medium for the heat exchange (e.g., the extraction liquid), the medium for the heat exchange (e.g., the extraction liquid), being introduced into the extraction reactor via the base-side supply after passing through the last heat exchanger element.

After the last heat exchanger element (i.e. in the extraction direction from the top to the bottom, the lowermost heat exchanger element contained in the extraction reactor) and in front of the base-side supply, a heat exchanger for temperature-control of the medium for the heat exchange, the extraction liquid, and/or a pump is arranged.

The heat exchanger or the pump is thereby contained in the connection line, which connects the individual heat exchanger elements which are connected successively in series, or is disposed therein.

Likewise, it can be provided that, in the case of such an arrangement of the individual heat exchanger elements (series connection), a heat exchanger is present, after each heat exchanger element, for temperature-control of the medium for the heat exchange (e.g., the extraction liquid).

The extraction reactor can be operated at ambient pressure or at excess pressure. For example, the pressure of the extraction reactor can be within a range of from about 1.0 bar absolute to about 3.0 bar absolute such as about 1.0 bar absolute to about 2.0 bar absolute.

The flow control of the heat transfer medium through the cassette bases can be effected in three variants (option 1, 2, 3, examples with respectively 4 control systems)):

Option 1: Throughflow with constant heat transfer medium temperature per cassette base or group of cassette bases:

Each individual cassette base (or groups of up to 6 cassette bases) is provided with a separate temperature control. As a function of the extract medium temperature in the individual compartments above the cassette bases, the flow quantity of the individual heat transfer medium is hereby regulated such that the extract medium temperature reaches the desired value. The temperature of the heat transfer medium thereby remains constant in the inflow.

Option 2: Throughflow with constant quantity of heat transfer medium:

Each individual cassette base (or groups of up to 6 cassette bases) is provided with a separate temperature control. As a function of the extract medium temperature above the cassette bases, the temperature of the individual heat transfer medium flow is hereby regulated such that the extract medium temperature in the individual compartments reaches the desired value. Either a 3-way mixing valve is hereby used which has a constant throughflow over the complete control range (see Figures) or a heat transfer medium circulation which is actuated with a pump over the cassette base with a constant overflow quantity and heat exchanger for temperature adjustment.

Option 3: Heat transfer medium control in counterflow with a proportional throughflow quantity:

The extraction liquid is used as heat transfer medium and firstly, in counterflow to the extraction liquid and in parallel flow to the polyamide granulate, is guided in series through the individual cassette bases [B] (see Figures). For adjustment of the temperature profile, the heat transfer medium can be heated or cooled between the individual cassette bases by the heat exchanger [C] (see Figures). After leaving the lowermost cassette base, the heat transfer medium is brought to extraction temperature in a heat exchanger [E] (see Figures) and, if necessary, is conducted into the extraction reactor [A] (see Figures) as extraction liquid with pump pressure [D] (see Figures). Since the quantity of extraction liquid is regulated proportionally to the fed-in quantity of granulate, the quantity of the heat transfer medium also remains proportional to the quantity of granulate. As a result, the temperature profile remains constant over the complete capacity range.

Mixed versions of the 3 options are also possible. The cassette bases [B] (see Figures) can be combined to form groups so that a temperature control system is formed for a group of 2 to 6, such as 2 to 3, cassette bases. The heat transfer medium is guided in series through the associated cassette bases.

The present disclosure likewise relates to a method for the extraction of monomeric or oligomeric components, which are soluble in an extraction liquid, for example, ε-caprolactam or oligomeric polyamide 6, from a granular material, for example, polyamide 6 granulate, or from a granulate of copolymers of polyamide 6 with a previously described extraction reactor according to the present disclosure in which granular material is fed into the vertically extending flow pipe via the at least one top-side inlet and is guided vertically downwards in the direction of the at least one base-side outlet and is removed there from the extraction reactor, an extraction liquid being fed into the vertically extending flow pipe via the at least one base-side supply and being guided in counterflow to the granular material in the direction of the at least one top-side outlet and being removed there, a vertical temperature gradient being produced in the flow pipe via the plurality of heat exchanger elements.

The extraction method according to the present disclosure is hence implemented by means of a vertical flow pipe for polyamide granulate. The granulate is guided from the top to the bottom in a filled bed. In counterflow to the granulate flow, a suitable extraction liquid is hereby guided, which absorbs monomers and oligomers from the granulate (extraction) and carries them with it from the reactor. The achievable extraction quality depends mainly upon the operating parameters of temperature, concentration in the extraction liquid, overflow rate and the dwell time.

In particular, it is provided with such a method control that temperatures in the flow pipe increasing, in the vertical direction, from the top to the bottom are set via the plurality of heat exchanger elements.

In an example, the temperature gradient is set such that the maximum temperature of the extraction liquid inside the flow pipe is, at any point, at least $0.5°$ C. to $10°$ C., such as $2°$ C. to $7°$ C., below the boiling point of the extraction liquid at the given hydrostatic pressure. In addition, the temperature control can be designed such that a prescribed maximum temperature is reached rapidly but never exceeded (for avoidance of material damage due to hydrolysis).

The pressure prevailing inside the flow pipe can be adjusted between 1.0 and 3.0 bar absolute, such as 1.0 and 2.0 bar absolute.

A corresponding pressure can be measured for example in the gas chamber at the top of the extraction reactor. The previously indicated pressures thereby denote the absolute pressure relative to absolute vacuum.

The method can be conducted in particular with the subsequently mentioned three variants, in which each heat exchanger element including (a) a separate inflow for a medium for the heat exchange which has a control valve via which the quantity of medium for the heat exchange, which flows through the respective heat exchanger element, can be regulated, each heat exchanger element being flowed through by an equally temperature-controlled medium for the heat exchange and the quantity of medium being varied per heat exchanger element or group of heat exchanger elements, (b) a first separate inflow for a first medium for the heat exchange and also a second separate inflow for a second medium for the heat exchange, first and second medium being temperature-controlled differently, respectively first and second inflow being connected in pairs to respectively one heat exchanger element via a three-way valve, a defined temperature being set by different mixing ratios of the first and second medium for each heat exchanger element or group of heat exchanger elements, or (c) a separate circulation for a medium for the heat exchange with circulation pump and heat exchanger, temperature and/or quantity of the medium being adjusted separately for each heat exchanger element or group of heat exchanger elements.

The temperature gradient can be set in particular by the plurality of heat exchanger elements, connected successively in series, being flowed through, beginning from the vertically uppermost heat exchanger element, by a medium for the heat exchange which can be the extraction liquid, the medium for the heat exchange, for example, the extraction liquid, being introduced into the extraction reactor via the base-side supply after passing through the last heat exchanger element and being heated, before introduction, to a predetermined extraction temperature prevailing at the base-side supply by means of a heat exchanger.

Adjustment of the temperature in the flow pipe operated in counterflow is effected by a plurality (4 to 30, such as 8 to 12) of baffle bases (e.g. cassette bases) which act as heat exchanger. As a result, the liquid temperature and hence also the granulate temperature can be adjusted in small steps so that an almost homogeneous temperature gradient over the length of the extraction reactor can be set.

Alternatively, a pipe coil construction which is flowed through by a heat transfer medium and acts as heat exchanger can be used. The cooling or heating of the extraction liquid flow is effected via a liquid heat transfer medium (e.g., water) which flows through the cassette bases on the inside.

As a result of the small-step temperature gradient, only small temperature differences are set over the flow baffles, which involve a small density difference over the flow baffles. Correspondingly, the driving force which could cause reversal of the flow is small.

The cassette bases can be combined to form groups so that a temperature control system is formed for a group of 2 to 6, such as 2 to 3, cassette bases. The heat transfer medium is guided in series through the associated cassette bases. The guidance of the heat transfer medium through the extraction reactor can be effected in 3 different variants (see option 1, 2, 3, examples with respectively 4 temperature control systems).

Option 1: Control via constant temperature:

Each individual cassette base (or groups of up to 6 cassette bases) is provided with a separate temperature control. As a function of the extract medium temperature above the cassette bases, the flow quantity of the individual heat transfer medium flows is hereby regulated such that the extract medium temperature reaches the desired value. The number of control systems is between 2 and the total cassette base number, such as between 4 and 6.

The temperature of the heat transfer media (12, 13, 14, 15) (see Figures) is below the respective extraction temperature (2, 3, 4, 5) (see Figures). The temperature in the granulate output region of the extraction reactor (1) (see Figures) is adjusted by the temperature of the extraction liquid (11) (see Figures). The output temperature of the extraction liquid (16) (see Figures) corresponds to a mix temperature of uppermost regulated extraction temperature (5) (see Figures) and the granulate input temperature (6) (see Figures).

Option 2: Control via constant throughflow quantity:

Each individual cassette base (or groups of up to 6 cassette bases) is provided with a separate temperature control. As a function of the extract medium temperature above the cassette bases, the temperature of the individual heat transfer medium flows is hereby regulated such that the extract medium temperature reaches the desired value. The number of control systems is between 2 and the total cassette base number, such as between 4 and 6.

When using mixer valves for temperature adjustment (example, option 2) in which the heat transfer medium temperature is mixed from a heating medium and a cooling medium, the temperature of the heating media is above the respective extraction temperature in the respective compartment. The temperature of the cooling media is below the respective extraction temperature in the respective compartment. The temperature in the granulate output region of the extraction reactor is set by the temperature of the extraction liquid. The output temperature of the extraction liquid corresponds to a mix temperature of uppermost controlled extraction temperature and the granulate input temperature.

Option 3: Heat transfer medium in counterflow with a proportional throughflow quantity:

The extraction liquid is used as heat transfer medium and, in counterflow to the extraction liquid and in parallel flow to the polyamide granulate, is guided in series through the individual cassette bases. For adjustment of the temperature profile, the heat transfer medium can be heated or cooled between the individual cassette bases by the heat exchanger. This takes place as a function of the extract medium temperature above the cassette base. After leaving the lowermost cassette base, the heat transfer medium is brought to extraction temperature in a heat exchanger and, if necessary, is conducted into the extraction reactor as extraction liquid with pump pressure. Since the quantity of extraction liquid is regulated proportionally to the fed-in quantity of granulate, also the quantity of heat transfer medium remains proportional to the quantity of granulate. As a result, the temperature profile remains constant over the complete capacity range.

The extraction temperature (2, 3, 4, 5) (see Figures) is formed respectively as mix temperature from the granulate temperature of the granulate entering from the top and from the extraction liquid temperature which enters from the bottom into the space temperature-controlled by the heated or cooled heat transfer medium. The temperature in the granulate output region of the extraction reactor (1) (see Figures) is set by the temperature of the heated extraction liquid (21) (see Figures). The output temperature of the extraction liquid (16) (see Figures) corresponds to a mix temperature of uppermost regulated extraction temperature (5) (see Figures) and of the granulate input temperature (6) (see Figures).

In particular, the extraction liquid can include one of water and a mixture of water and $\epsilon$-caprolactam and/or a the medium for the heat exchange can include one of water, a mixture of water and an alcohol which is miscible with water, and a mixture of water and $\epsilon$-caprolactam.

The present disclosure is explained in more detail with reference to the subsequent embodiments and also the accompanying Figures without however restricting the present disclosure to the represented parameters.

BRIEF DESCRIPTION OF THE DRAWINGS

In the drawings, which are not necessarily drawn to scale, like numerals can be used to describe similar components in different views. The drawings illustrate generally, by way of example, but not by way of limitation, various embodiments discussed in the present patent document.

DETAILED DESCRIPTION

Figure 1:
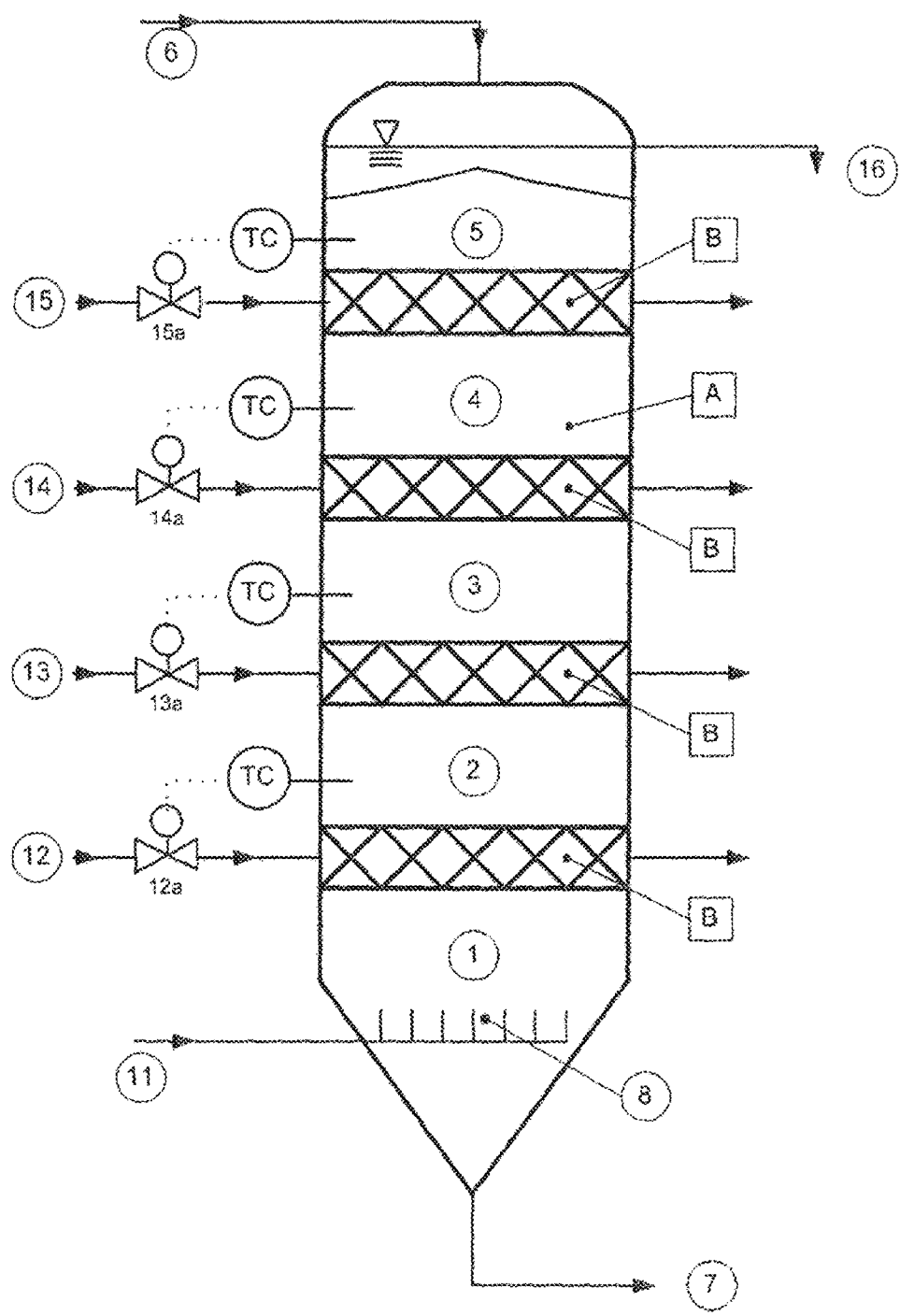
FIG. 1 illustrates a first example of an extraction reactor according to the present disclosure.

FIG. 1 shows a first embodiment of an extraction reactor according to the present disclosure. The extraction reactor thereby comprises a vertically disposed flow pipe A in which a plurality of heat exchanger elements B, which extend in the vertical direction and are in total four in the example of FIG. 1, are inserted. The heat exchanger elements thereby fill the complete cross-section of the flow pipe A. In FIG. 1, the heat exchanger elements B are disposed equidistantly. By means of the heat exchanger elements B, the flow pipe A is subdivided into individual compartments 1, 2, 3, 4, 5. The extraction reactor has a top-side inlet 6 via which granular material, for example PA6 granulate, can be supplied to the extraction reactor. The granular material supplied at the top-side can flow through the extraction reactor from the top to the bottom, thereby undergoes extraction in the extraction reactor and leaves the extraction reactor at the base-side outlet 7. In addition, the extraction reactor has an inlet 8, disposed at the base-side, for extraction liquid 11, the base-side inlet 8 being disposed after the last heat exchanger element, i.e. as lowermost element in the extraction reactor. Via the inflow 8 for extraction liquid 11, extraction liquid 11 can be fed into the extraction reactor at the base-side. The extraction liquid thereby flows through the extraction reactor from the bottom to the top and is removed again from the extraction reactor via an outflow or outlet 16 disposed at the top-side. Hence, an extraction can be effected in counterflow with an extraction reactor according to the present disclosure.

According to the example according to FIG. 1, it is now provided that each heat exchanger element B can be flowed through by a heat-exchanging medium via a separate inflow 12, 13, 14, 15. Each heat exchanger element B likewise has a separate outflow for a corresponding heat-exchanging fluid. Regulation of the quantity of heat-exchanging medium which flows through a respective heat exchanger element B can be thereby controlled for each inflow 12, 13, 14, 15 by means of a separate valve 12a, 13a, 14a, 15a. Each valve can be controlled for example also via a temperature sensor TC so that, in each compartment 2, 3, 4, 5, for example predefined temperatures can be set and, by regulation of the throughflow or of the temperature of a heat-exchanging fluid flowing through a respective heat exchanger element B, the predefined temperature in the compartment can be adjusted.

Figure 2:
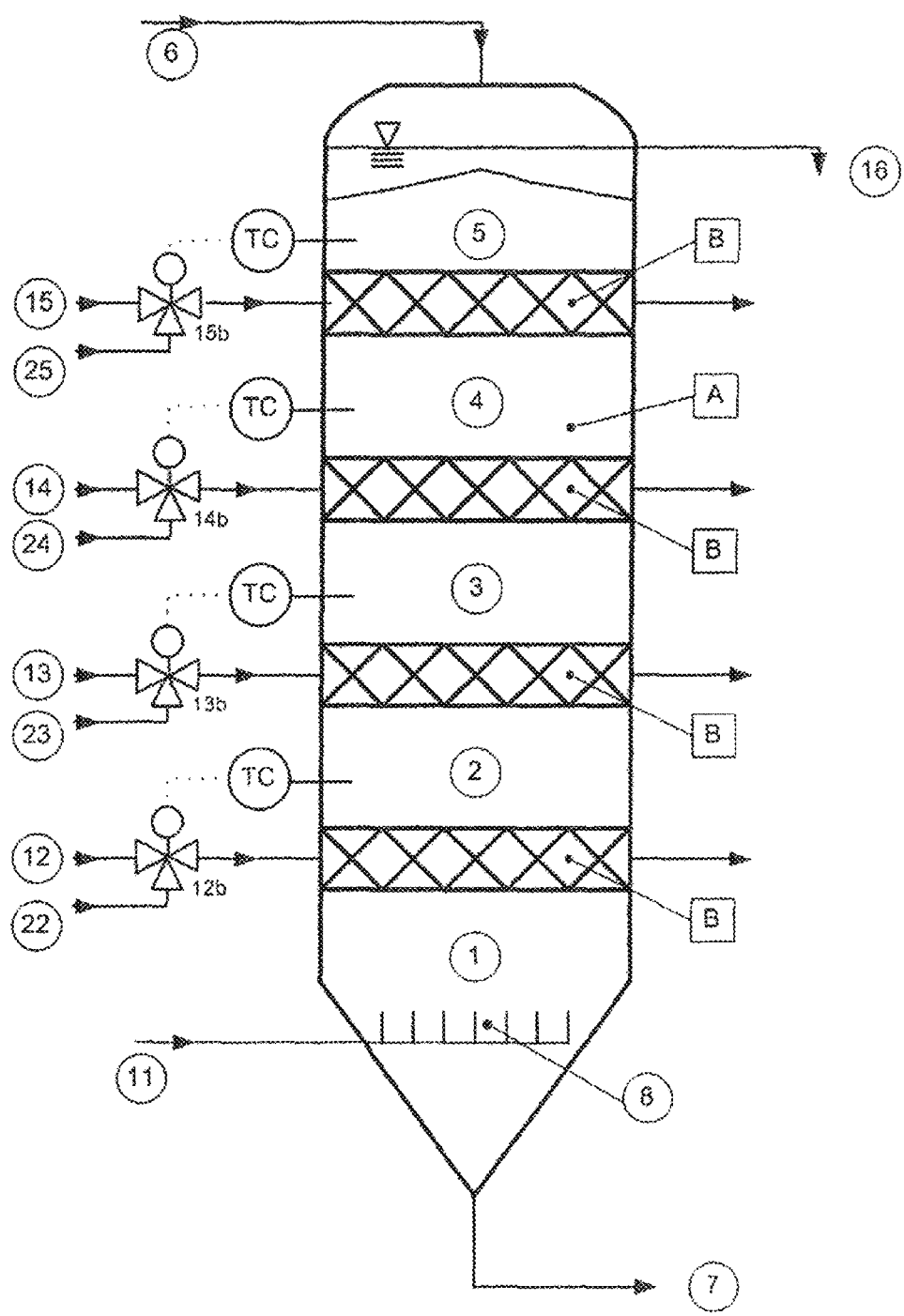
FIG. 2 illustrates a second example of an extraction reactor according to the present disclosure.

FIG. 2 shows a further example of an extraction reactor according to the present disclosure. The same elements are thereby described with the same reference numbers as also already used in FIG. 1. In contrast to the embodiment according to FIG. 1, the extraction reactor according to FIG. 2 differs in a different provision or supply of the heat exchanger elements B with heat-exchanging media. Each heat exchanger element B thereby has two separate inflows 12 and 22, 13 and 23, 14 and 24 or 15 and 25, with which respectively two different media for the heat exchange can be supplied to the respective heat exchanger element B. For example it can be provided that the temperature of the first medium 12, 13, 14, 15 is higher than the temperature of the second medium 22, 23, 24, 25. Via the respective mixing ratio of both first and second media which are supplied via the respective inflows 12 and 22, 13 and 23, 14 and 24, and 25, which ratio can be adjusted via a corresponding three-way valve or mixing valve 12b, 13b, 14b, 15b, the respective heat exchanger elements B can be temperature-controlled differently. The total quantity of media, which is thereby guided through the heat exchanger elements B respectively, can thereby be kept constant but also be varied.

Figure 3:
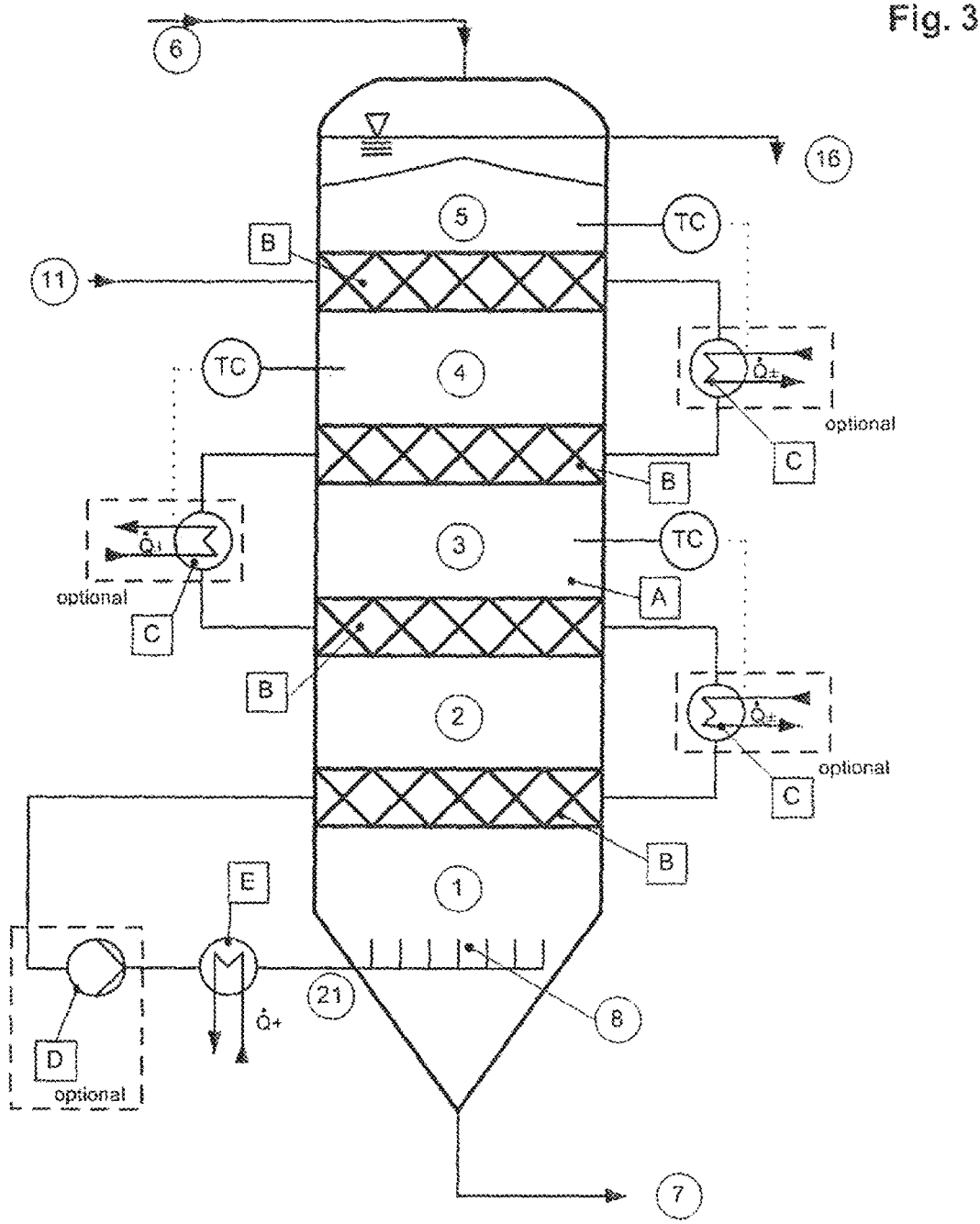
FIG. 3 illustrates a third example of an extraction reactor according to the present disclosure.

FIG. 3 shows a further example of an extraction reactor according to the present disclosure. Here also, the same reference numbers denote the same elements as described already in the preceding Figures. Also the embodiment according to FIG. 3 differs from the preceding embodiments by a different supply of the respective heat exchanger elements B with heat-exchanging media. In the case of the example of FIG. 3, the heat-exchanging medium thereby flows through the individual heat exchanger elements B in series, beginning with the uppermost heat exchanger element. After passing though the last heat exchanger element B, the heat-exchanging medium is thereby supplied to the extraction reactor via the base-side inlet 8. According to the example of FIG. 3, the heat-exchanging medium which is used is hence the extraction liquid 11. After passing through the first heat exchanger element B, disposed uppermost, the heat-exchanging medium or the extraction liquid 11 is supplied to the second heat exchanger element B via a separate pipeline. In this pipeline, i.e. between the first and the second heat exchanger element B, a heat exchanger C can thereby be disposed, with which temperature-control of the heat-exchanging medium or of the extraction liquid 11 can be effected. In addition, the extraction reactor according to FIG. 3 has a pump D which is disposed in the liquid flow of the heat-exchanging medium or of the extraction liquid 11. A further heat exchanger E is likewise connected subsequent to the pump D.

Figure 4:
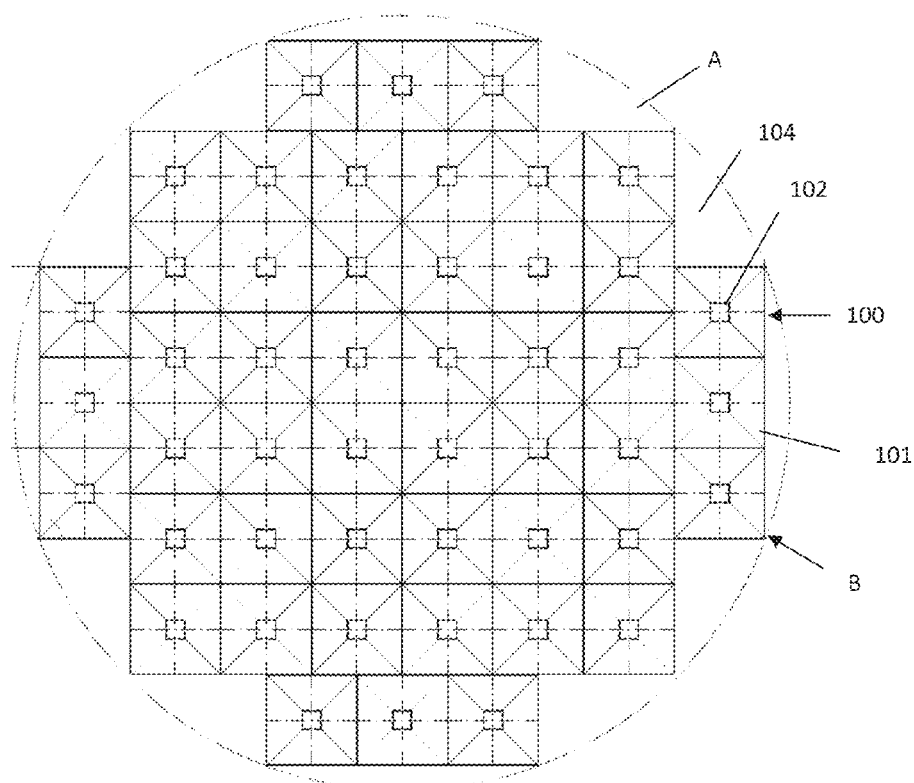
FIG. 4 illustrates a cassette base which can be used in an extraction reactor according to the present disclosure in plain view.
Figure 5:
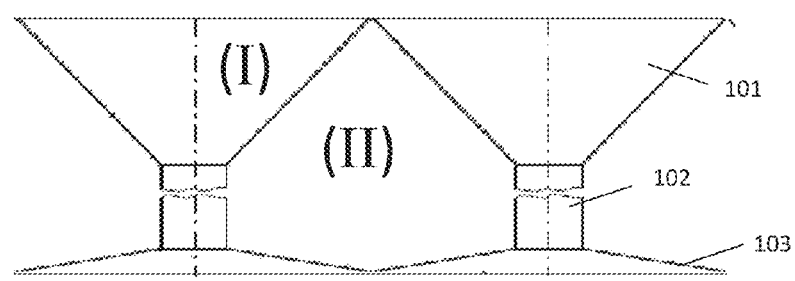
FIG. 5 illustrates a cross-section through individual flow elements of a cassette base illustrated in FIG. 4.

FIGS. 4 and 5 show a cassette base which can be used as heat exchanger element B in an extraction reactor, as illustrated for example in FIGS. 1 to 3. In FIG. 4, a plan view from the top onto a corresponding cassette base is illustrated, whilst a cross-section through two individual flow elements is illustrated in FIG. 5. In FIG. 4, an embodiment is illustrated in which a corresponding cassette base is introduced into a flow pipe A, filling the cross-section. The cassette base B thereby comprises a plurality of individual flow elements 100, which are joined together, 48 items in the case of the example of FIG. 4, and fill the entire area of the flow pipe. The regions 104 which are not filled by the flow elements 100 can thereby be closed by a continuous metal sheet so that any liquid or granulate flowing through the pipe must necessarily be guided through an individual flow element 100 of a corresponding cassette base B. Each individual flow element thereby has a cone 101 via which an inflow into an individual flow element 100 takes place from the top to the bottom in the flow direction. The cone 101 opens into a through-tunnel 102, this in turn opens into a likewise conical outlet 103. In the embodiment according to FIG. 4, given by way of example, all the individual flow elements 100 have a square plan view (see FIG. 4), however a different geometry of the individual flow elements 100 is likewise conceivable, for example a hexagonal geometry.

As a result of the tapering of the cone 101 into the through-tunnel 102, a space I is produced between the entry- and exit surface of the individual flow elements, through which space for example the granulate or the extraction liquid is guided, and also an intermediate space II through which a temperature-controlling medium can be guided. Via the heating medium space II, temperature-control of the cassette base can hence be effected.

Figure 6:
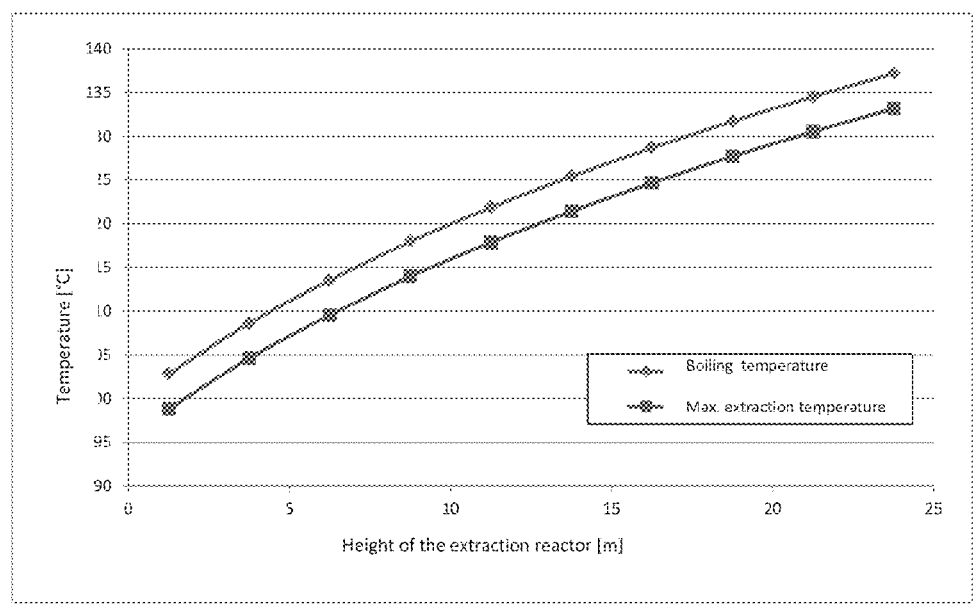
FIG. 6 illustrates a temperature gradient which can be produced over the entire height with an extraction reactor according to the present disclosure.

FIG. 6 shows a temperature gradient which can be achieved with an extraction reactor according to the present disclosure. Such an extraction reactor thereby has 10 heat exchanger elements B via which respectively temperature-control of the extraction liquid can be achieved. On the abscissa, the height of the extraction reactor in meters is indicated, the height is thereby measured from top to bottom. On the ordinate, the theoretical boiling temperature of the extraction medium which is used is indicated (upper measurement curve) which, as illustrated, increases with the hydrostatic pressure of the extraction medium with increasing height downwards. The lower curve thereby denotes the actually set extraction temperature of the extraction medium which is temperature-controlled via the respective heat exchanger elements B.

EXAMPLES

Example 1

Use of an extraction column according to pos. 1 in which the extraction liquid is guided from the top to the bottom through all the cassettes of the extraction column in parallel flow to the granulate (cassette flow). After discharge of the extraction liquid, the latter is heated by a heat exchanger to input temperature. Conveyance of the extraction liquid takes place by means of a centrifugal pump.

Alternatively, the extraction liquid can be guided directly into the main extraction chamber without being guided in advance through the cassette bases. The cassette bases consequently exert no cooling or heating influence. The extraction column has 6 cassette bases. Between cassette 3 and 4 (counted from the bottom), the cassette flow can be heated by means of a tubular heat exchanger by heating steam. Temperature gauges are installed below the lowermost cassette base and above each cassette base. The temperatures and the extract content granulate percentage after extraction is provided in Table I.
Installation:
Extractor diameter: 600 mm
Number of cassette bases: 6 items
Number of cassette elements per cassette base: 4 items
Spacing of the cassette bases: equidistant
Granulate flow: 60 kg/h
Extraction liquid flow: 65 kg/h
Dwell time granulate in extractor: ~13 h
Extract content in the granulate before extraction: 9.2%
Extract content of the extraction liquid before extraction: ~0.0%
Temperature granulate in the inflow: 95° C.

TABLE I

|  | Operation without cassette flow | Operation with cassette flow without intermediate heating | Operation with cassette flow with intermediate heating |
|---|---|---|---|
| inflow extraction liquid cassette bases | — | 99.5° C. | 99.5° C. |
| outflow extraction liquid | 98° C. | 97.5° C. | 98° C. |
| temperature above cassette 6 | 98° C. | 97° C. | 98° C. |
| temperature above cassette 5 | 99° C. | 98° C. | 99° C. |
| temperature above cassette 4 | 100° C. | 99° C. | 101° C. |
| temperature above cassette 3 | 100° C. | 100° C. | 104.5° C. |
| temperature above cassette 2 | 101° C. | 101° C. | 106° C. |
| temperature above cassette 1 | 102° C. | 103° C. | 107° C. |
| inflow extraction liquid main extractor | 102° C. | 111° C. | 111° C. |
| temperature granulate outflow | 102° C. | 108° C. | 110° C. |
| extract content granulate after extraction | 0.8% | 0.6% | 0.3% |

Example 2

Use of an extraction column according to pos. 10 in which the extraction liquid is guided from the top to the bottom through all the cassettes of the extraction column in parallel flow to the granulate (cassette flow). After discharge of the extraction liquid, the latter is heated by a heat exchanger to input temperature. Conveyance of the extraction liquid takes place by means of a centrifugal pump.

Alternatively, the extraction liquid can be guided directly into the main extraction chamber without being guided in advance through the cassette bases. The cassette bases consequently exert no cooling or heating influence. The extraction column has 9 cassette bases. Between cassette 3 and 4, and also 6 and 7 (counted from the bottom), the cassette flow can be heated by means of tubular heat exchangers by heating steam. Temperature gauges are installed below the lowermost cassette base and above each cassette base. The temperatures and the extract content granulate percentage after extraction are provided in Table II.
Installation
Extractor diameter: 2,000 mm
Number of cassette bases: 9 items
Number of cassette elements per cassette base: 16 items
Granulate flow: 2,500 kg/h
Extraction liquid flow: 65 kg/h
Dwell time granulate in extractor: ~11 h
Extract content in the granulate before extraction: 9.2%
Extract content of the extraction liquid before extraction: ~0.0%
Temperature granulate in the inflow: 98° C.

TABLE II

|  | Operation without cassette flow | Operation with cassette flow without intermediate heating | Operation with cassette flow with intermediate heating |
|---|---|---|---|
| inflow extraction liquid cassette bases | — | 95° C. | 95° C. |
| outflow extraction liquid | 98° C. | 98° C. | 98° C. |
| inflow extraction liquid main extractor | 102° C. | 128° C. | 128° C. |
| Temperature granulate outflow | 102° C. | 121° C. | 125° C. |
| extract content granulate after extraction | 0.4% | 0.2% | 0.13% |

The above Detailed Description includes references to the accompanying drawings, which form a part of the Detailed Description. The drawings show, by way of illustration, specific embodiments in which the present surgical cutting guide systems and methods can be practiced. These embodiments are referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the present disclosure should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." The terms "including" and "comprising" are open-ended, that is, a system or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. An extraction reactor, for liquid extraction from granular material, comprising:
    at least one vertically extending flow pipe including a plurality of horizontally configured heat exchanger elements that fill a cross-section of the at least one vertically extending flow pipe completely or partially and that can be flowed through by the granular material and the extraction liquid, the plurality of heat exchanger elements subdividing the at least one vertically extending flow pipe into individual vertical compartments;
    at least one top-side inlet for the granular material;
    at least one base-side outlet for the granular material;
    at least one base-side supply for the extraction liquid; and
    at least one top-side outlet for the extraction liquid,
wherein the plurality of heat exchanger elements are arranged to form groups of heat exchanger elements, by the heat exchanger elements for each group, connected successively in series, being flowed through, beginning with the vertically uppermost heat exchanger element of each group, by a medium for heat exchange.

2. The extraction reactor claim 1, wherein at least two to thirty heat exchanger elements are present.

3. The extraction reaction of claim 1, wherein the plurality of heat exchanger elements are disposed in a vertical direction and positioned equidistant from each other, and/or at a different spacing from each other.

4. The extraction reactor of claim 1, wherein the plurality of heat exchanger elements are selected from the group consisting of cassette bases, baffle bases, pipe coil constructions and combinations hereof.

5. The extraction reactor of claim 4, wherein the cassette bases comprise between nine and ninety-six individual flow elements that have respectively a separate space for the granular material and the extraction liquid and a connected space for a medium for the heat exchange.

6. The extraction reactor of claim 5, wherein the individual flow elements have a square or hexagonal cross-section in the flow direction/vertical direction and a conical granulate inflow, a through-tunnel, and a conical granulate outlet.

7. The extraction reactor of claim 1, wherein the at least one base-side supply for the extraction liquid comprises a liquid distributor with which the extraction liquid can be distributed over the entire cross-section of the flow pipe.

8. The extraction reactor of claim 1, wherein at least some or all of the individual vertical compartments have a temperature sensor ($T_c$) for determining a temperature of the granular material and/or of the extraction liquid present in a respective individual vertical compartment.

9. The extraction reactor of claim 1, wherein each heat exchanger element of the plurality of heat exchanger elements includes one of:
    a separate inflow for a medium for heat exchange, which has a control valve via which the quantity of the medium for the heat exchange, which flows through the respective heat exchanger element, can be regulated;
    a first separate inflow for a first medium for the heat exchange and a second separate inflow for a second medium for the heat exchange, the first and second mediums being temperature-controlled differently respectively the first and second separate inflows being connected in pairs to respectively one heat exchanger element via a three-way valve; and
    a separate circulation for a medium for the heat exchange with circulation pump and heat exchanger.

10. An extraction reactor, for liquid extraction from granular material, comprising:
    at least one vertically extending flow pipe including a plurality of horizontally configured heat exchanger elements that fill a cross-section of the at least one vertically extending flow pipe completely or partially and that can be flowed through by the granular material and extraction liquid, the plurality of heat exchanger elements subdividing the at least one vertically extending flow pipe into individual vertical compartments;
    at least one top-side inlet for the granular material;
    at least one base-side outlet for the granular material;
    at least one base-side supply for the extraction liquid; and
    at least one top-side outlet for the extraction liquid,
wherein the plurality of heat exchanger elements, connected successively in series, is flowed through, beginning from a vertically uppermost heat exchanger element, by a medium for heat exchange, the medium for the heat exchange being introduced into the extraction reactor via the at least one base-side supply after passing through a last heat exchanger element.

11. The extraction reactor of claim 10, wherein, after the last heat exchanger element and in front of the at least one base-side supply, a heat exchanger is arranged for temperature-control of the medium for the heat exchange.

12. The extraction reactor of claim 11, wherein, after an individual or each heat exchanger element, a heat exchanger is present for temperature-control of the medium for the heat exchange.

13. A method for the extraction of monomeric or oligomeric components, which are soluble in an extraction liquid from a granular material or from a granulate of copolymers of polyamide 6 with the extraction reactor of claim 1, the method comprising:
    feeding granular material into the vertically extending flow pipe via the at least one top-side inlet and is guided vertically downwards in a direction of the at least one base-side outlet and is removed there from the extraction reactor; and
    feeding an extraction liquid into the vertically extending flow pipe via the at least one base-side supply and being guided in counterflow to the granular material in a direction of the at least one top-side outlet and being removed there, wherein a vertical temperature gradient is produced in the flow pipe via the plurality of heat exchanger elements.

14. The method of claim 13, wherein temperatures in the flow pipe increase, in the vertical direction, from the top to the bottom are set via the plurality of heat exchanger elements.

15. The method of claim 13, wherein the temperature gradient is set such that the maximum temperature of the extraction liquid inside the flow pipe is, at any point, at least 0.5° C. to 10° C. below a boiling point of the extraction liquid at a given hydrostatic pressure.

16. The method of claim 13, wherein, in at least one of the individual vertical compartments of the flow pipe, a maximum extraction temperature is reached, which is no longer exceeded thereafter until discharge of the extraction liquid.

17. The method of claim 13, wherein the pressure inside the flow pipe is between 1.0 and 3.0 bar absolute.

18. The method of claim 13, wherein the temperature gradient is set by each heat exchanger element including one of:
   a separate inflow for a medium for heat exchange which has a control valve via which the quantity of the medium for the heat exchange, which flows through the respective heat exchanger element, can be regulated, each heat exchanger element being flowed through by an equally temperature-controlled medium for the heat exchange and the quantity of medium being varied per heat exchanger element or group of heat exchanger elements;
   a first separate inflow for a first medium for the heat exchange and also a second separate inflow for a second medium for the heat exchange, first and second mediums being temperature-controlled differently, respectively first and second inflows being connected in pairs to respectively one heat exchanger element via a three-way valve, a defined temperature being set by different mixing ratios of the first and second mediums for each heat exchanger element or group of heat exchanger elements; and
   a separate circulation for a medium for the heat exchange with circulation pump and heat exchanger, temperature and/or quantity of the medium being set separately for each heat exchanger element or group of heat exchanger elements.

19. The method of claim 13, wherein the temperature gradient is set by the plurality of heat exchanger elements, connected successively in series, being flowed through, beginning from the vertically uppermost heat exchanger element, by a medium for the heat exchange, the medium for the heat exchange being introduced into the extraction reactor via the base-side supply after passing through the last heat exchanger element and being heated, before introduction, to a predetermined extraction temperature prevailing at the base-side supply by means of a heat exchanger.

20. The method of claim 13, wherein the extraction liquid includes at least one of water and a mixture of water and ϵ-caprolactam, and wherein the medium for the heat exchange includes at least one of water, a mixture of water and an alcohol which is miscible with water, and a mixture of water and ϵ-caprolactam.

* * * * *